US012344858B2

(12) United States Patent
Huh et al.

(10) Patent No.: US 12,344,858 B2
(45) Date of Patent: Jul. 1, 2025

(54) TARGETED GENOME MODIFICATION USING CIRCULAR SINGLE-STRANDED DNA

(71) Applicant: FULL CIRCLES THERAPEUTICS, INC., Cambridge, MA (US)

(72) Inventors: Jin Hang Huh, Watertown, MA (US); Qun Shan, Belmont, MA (US)

(73) Assignee: FULL CIRCLES THERAPEUTICS, INC., Cambridge, MA (US)

( * ) Notice: Subject to any disclaimer, the term of this patent is extended or adjusted under 35 U.S.C. 154(b) by 893 days.

(21) Appl. No.: 17/365,330

(22) Filed: Jul. 1, 2021

(65) Prior Publication Data
US 2021/0340571 A1 Nov. 4, 2021

Related U.S. Application Data

(63) Continuation of application No. PCT/US2020/012244, filed on Jan. 3, 2020.

(60) Provisional application No. 62/788,379, filed on Jan. 4, 2019.

(51) Int. Cl.
C12N 15/87 (2006.01)
A61K 35/17 (2025.01)
A61K 40/31 (2025.01)
C07K 14/725 (2006.01)
C12N 9/22 (2006.01)
C12N 15/90 (2006.01)

(52) U.S. Cl.
CPC ............. C12N 15/87 (2013.01); A61K 35/17 (2013.01); A61K 40/31 (2025.01); C07K 14/7051 (2013.01); C12N 9/22 (2013.01); C12N 15/90 (2013.01); A61K 2239/10 (2023.05); C12N 2310/20 (2017.05); C12N 2510/00 (2013.01); C12N 2795/14043 (2013.01)

(58) Field of Classification Search
CPC ...... C12N 15/87; C12N 9/22; C12N 2510/00; C12N 2310/20; C12N 2795/00043; C12N 15/11; C12N 9/16; C12N 15/90; C12N 15/85; C12N 2795/14043; A61K 35/17; A61K 31/7088; C07K 14/7051; C07K 2319/60
USPC ...... 435/455, 463, 328, 199; 536/23.1, 23.4, 536/24.2; 530/387.3, 358
See application file for complete search history.

(56) References Cited

U.S. PATENT DOCUMENTS

2002/0099196 A1 7/2002 Hiraoka et al.
2018/0127785 A1 5/2018 Junge et al.

FOREIGN PATENT DOCUMENTS

WO 2016196887 A1 12/2016
WO WO-2017152015 A1 * 9/2017 ............. A61K 35/17
WO 2017184768 A1 10/2017
WO 2019/213504 A1 11/2019

OTHER PUBLICATIONS

Carroll D, Beumer KJ. Genome engineering with TALENs and ZFNs: repair pathways and donor design. Methods. Sep. 2014;69(2):137-41. Epub Apr. 2, 2014. (Year: 2014).*
Moriya M. Single-stranded shuttle phagemid for mutagenesis studies in mammalian cells: 8-oxoguanine in DNA induces targeted G.C-->T.A transversions in simian kidney cells. Proc Natl Acad Sci U S A. Feb. 1, 1993;90(3):1122-6. (Year: 1993).*
Yoshimi K, Kunihiro Y, Kaneko T, Nagahora H, Voigt B, Mashimo T. ssODN-mediated knock-in with CRISPR-Cas for large genomic regions in zygotes. Nat Commun. Jan. 20, 2016;7:10431. (Year: 2016).*
Li, H. et al. "Design and specificity of long ssDNA donors for CRISPR-based knock-in" bioRxiv, Aug. 21, 2017, XP055869818, DOI: 10.1101/178905. 24 pages.
Miura, H. et al. "Easi-CRISPR for creating knock-in and conditional knockout mouse models using long ssDNA donors" Nature Protocols, 2018, vol. 13, No. 1, pp. 195-215.
Roth, T. et al. "Reprogramming human T cell function and specificity with non-viral genome targeting" Nature, Jul. 19, 2018; vol. 559; 31 pages.
Supplementary European Search Report for European Application No. 20736081. Mail Date: Sep. 16, 2022. 4 pages.
Chen et al. "CRISPR-Cas12a target binding unleashes indiscriminate single-stranded DNase activity" Science, Feb. 15, 2018, vol. 260, pp. 436-439.
International Search Report mailed Mar. 18, 2020 in International Application No. PCT/US2020/012244. 3 pages.
Iyer et al. "Efficient Homology-directed Repair with Circular ssDNA Donors" BioRxiv, Dec. 5, 2019, pp. 1-42.
Nafisi et al. "Construction of a novel phagemid to produce custom DNA origami scaffolds" Synthetic Biology, 2018, 3(1), 8 pages.
Shepherd et al. "Bioproduction of pure, kilobase-scale single-stranded DNA" Sci Rep, Apr. 16, 2019, vol. 9, 9 pages.
Eyquem, Justin , et al., "Targeting a CAR to the TRAC locus with CRISPR / Cas9 enhances tumour rejection", Nature, vol. 543, Mar. 2, 2017, pp. 113-117.
Chowdhury, Dipanjan, et al. "The Exonuclease TREX1 Is in the SET Complex and Acts in Concert with NM23-H1 to Degrade DNA during Granzyme A-Mediated Cell Death" Molecular Cell 23, Jul. 7, 2006, pp. 133-142.
Fujioka, Ken-ichiro, et al. "Targeted recombination with single-stranded DNA vectors in mammalian cells" Nucleic Acids Research, 1993, vol. 21, No. 3, pp. 407-412.

(Continued)

Primary Examiner — Anne Marie S Wehbe
Assistant Examiner — Katie L Pennington
(74) Attorney, Agent, or Firm — Perkins Coie LLP; Viola Kung

(57) ABSTRACT

The present invention is directed to methods for generating one or more genetically modified cells by using a circular single stranded DNA (CiSSD) as a donor template and targeting genome modification. These methods include transferring one or more DNA polynucleotides into the cell for site-specific nuclease-mediated DNA repair and selecting one or more cells having the transferred DNA incorporated into the cell's genome.

14 Claims, 3 Drawing Sheets

Specification includes a Sequence Listing.

(56) References Cited

OTHER PUBLICATIONS

Gersbach, Charles A., et al. "Targeted plasmid integration into the human genome by an engineered zinc-finger recombinase" Nucleic Acids Research, Jun. 7, 2011, vol. 39, No. 17, pp. 7868-7878.

Huang, Kuan-Wei, et al. "Identification of Inhibitors for the DEDDh Family of Exonucleases and a Unique Inhibition Mechanism by Crystal Structure Analysis of CRN-4 Bound with 2-Morpholin-4-ylethanesulfonate (MES)" Journal of Med. Chem, 2016, pp. 8019-8029.

Katic, Iskra, et al. "CRISPR/Cas9 Genome Editing in Caenorhabditis elegans: Evaluation of Templates for Homology-Mediated Repair and Knock-Ins by Homology-Independent DNA Repair" G3, Genes, Genomes, Genetics, vol. 5, No. 1, Aug. 2015, pp. 1649-1656.

Le Moigne, Vincent, et al. "Homologous Recombination with Linear DNA to Insert Antigenic Protein in the Flagellin: Improvement of the Th1 Immune Response" Microbiology Immunology Journal, Oct. 6, 2006, vol. 152, Issue 11, pp. 33-43.

Sharan, Shyam K., et al. "Recombineering: a homologous recombination-based method of genetic engineering" Journal of Nature Protocols, Jan. 29, 2009, vol. 4 No. 2, pp. 206-223.

Yu, Daiguan, et al. "An efficient recombination system for chromosome engineering in *Escherichia coli*" PNAS, May 23, 2000, vol. 97 No. 11, pp. 5917-5983.

\* cited by examiner

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
ggtagtcgta ctcgtcgtcg                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
ggtagctagg agttccagga c                                            21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
acgatgtggg agaaggcagt c                                            21
```

TARGETED GENOME MODIFICATION USING CIRCULAR SINGLE-STRANDED DNA

This application is a continuation of PCT/US2020/012244, filed Jan. 3, 2020; which claims the benefit of U.S. Provisional Application No. 62/788,379, filed Jan. 4, 2019. The contents of the above-identified applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of 2020-01-03_Sequence-Listing_ST25-1319048001WO1.txt with a creation date of Jan. 3, 2020, and a size of 1 kilobyte. The Sequence Listing filed via EFS-Web is part of the specification and is hereby incorporated in its entirety by reference herein.

FIELD OF THE INVENTION

The present invention relates to using circular single-stranded DNA (CiSSD) as donor templates for targeted genome modification.

BACKGROUND OF THE INVENTION

Single-stranded (ss) deoxyribonucleic acid (DNA) have recently been shown more effective than double stranded (ds) DNA as donor templates for targeted genome modification in CRISPR-based genome editing.[1-8] Specifically, ssDNA templates outperform duplex templates in several important aspects, namely improved efficiency, enhanced specificity, and reduced cytotoxicity.[7] The ssDNA templates used in these studies are linear single-stranded DNA (LiSSD) produced with in vitro methods,[1] which are inherently error-prone, inefficient, expensive, and limited to carrying short DNA sequences of less than 2 kb.

Many genome-editing technologies require DNA sequences in excess of 2 kb, which cannot be achieved using these linear ssDNA templates. There is a need for DNA templates capable of carrying sequences in excess of 2 kb for use in cellular engineering. The new DNA templates should have low error rates, be efficient, specific, and low cytotoxic.

DETAILED DESCRIPTION OF THE INVENTION

Figure 1:
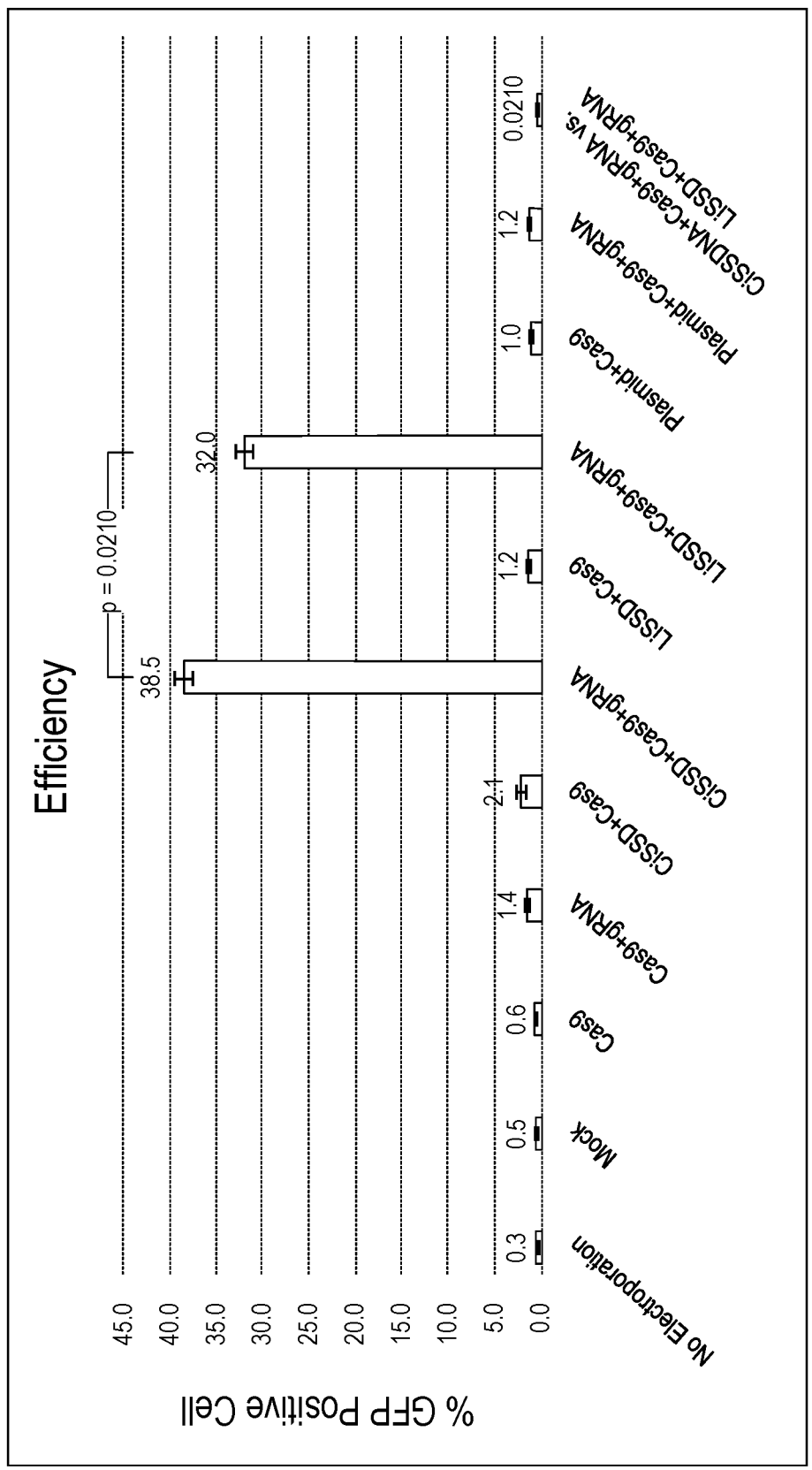
FIG. 1 is a chart showing the efficiency of insertion using CiSSD vs LiSSD in the noted conditions. Efficiency is measured by the percentage of GFP positive cells.

The present invention is directed to methods for generating one or more genetically modified cells by using a circular single stranded DNA (CiSSD) as a donor template and targeted genome modification.

The method comprises the steps of: (a) transferring a CiSSD having a DNA insert, a 5' homology arm, and a 3' homology arm to a cell, wherein the 5' homology arm and the 3' homology arm are complementary to the polynucleotides in a target region of a genomic DNA in the cell; (b) inducing a nucleotide break in the target region of genomic DNA in the cell; (c) hybridizing the 5' homology arm and the 3' homology arm of the CiSSD with the complementary polynucleotides in the target region of the genomic DNA, (d) inserting the DNA insert into the target region of genomic DNA, whereby one or more genetically modified cells is generated.

In step (a), the CiSSD having a DNA insert, a 5' homology arm, and a 3' homology arm, is transferred to a cell. In certain preferred embodiments, the DNA insert is an exogenous DNA insert. The term "exogenous" as used herein refers to a nucleic acid or polynucleotide indicates that is not in its native environment. Here, the exogenous DNA insert is exogenous to the genetically modified cell. For example, the exogenous DNA insert may be a sequence from one species that is introduced into a cell from another species (the cell to be modified), or it can be a sequence that is native to the cell that will be genetically modified that is reintroduced. An exogenous nucleic acid that includes a native sequence and has been reintroduced can often be distinguished from the naturally-occurring sequence by the presence of non-natural sequences linked to the exogenous nucleic acid, e.g., a nucleotide sequence encoding a reporter (e.g., a fluorescent reporter or an antibiotic reporter).

In step (a), the DNA insert is located between the 5' homology arm and the 3' homology arm which are complementary to the polynucleotides in a target region of a genomic DNA in the cell. Homology arms as used herein refer to a series of nucleotides that are complementary to a series of nucleotides in an endogenous DNA sequence in the target region. The homology arms flanking the DNA insert allow for specific insertion of the DNA insert in the target region. A target region is a nucleic acid sequence where a desired insertion or modification occurs.

In certain embodiments, the DNA insert is at least 1 nucleotide. In certain embodiments, the DNA insert is at least about 0.5 kb, 2 kb, 2.5 kb, 5 kb, 10 kb, 20 kb, 40 kb, 80 kb, 100 kb, 150 kb, or 200 kb. "About" as used in this application, refers to +10% of the recited value.

In certain embodiments, the length of the DNA insert is about 0.5 kb to 5 kb, about 1 kb to 5 kb, about 1 kb to 10 kb, about 1.6 kb to 5 kb, about 1.6 kb to 10 kb, about 2 kb to 5 kb, about 2 kb to 20 kb, about 2.5 kb to 5 kb, about 2.5 kb to 10 kb, about 2.5 kb to 20 kb, and about 5 kb to 100 kb.

In some embodiments, the DNA insert size may range from about 1 kb to about 3 kb, about 3 kb to about 6 kb, about 6 kb to about 9 kb, about 9 kb to about 12 kb, about 12 kb to about 15 kb, about 15 kb to about 18 kb, or about 18 kb to about 21 kb.

In some embodiments, the DNA insert may comprise a nucleotide sequence that encodes a maker or a reporter, e.g., a fluorescent marker, an antibiotic marker, or any suitable marker. A "marker" or "reporter" as used herein means a feature that allows for identification and selection of a desired cell, e.g., by fluorescence or antibiotic resistance. For example, the insert may include a nucleotide sequence encoding a reporter (e.g., GFP, RFP, or any suitable reporter) or a recombinase. For example, the reporter is an N-terminal GFP fusion reporter.

In some embodiments, the DNA insert may comprise a nucleotide sequence that encodes a transcription unit, wherein each transcription unit can produce a cellular product (e.g., protein or RNA). In some embodiments, the DNA insert may comprise a nucleotide sequence that encodes a protein, e.g., an immunomodulatory protein (e.g., a cytokine), an antibody, a chimeric antigen receptor (CAR), a growth factor, a T cell receptor, or another protein.

In step (b), a nucleotide break in the target region of genomic DNA is introduced in the cell. In certain embodiments, the break is a double stranded break (DSB). In certain embodiments, the break is a single-stranded DNA break or a nick. Precision gene editing techniques, e.g., CRISPR, create a break near a desired sequence change (target sequence).[32] CRISPR can be applied to produce deletions, disruptions, insertions, replacements, and repairs. The components of template donors for these different modifications is generally the same, consisting of three basic elements: a 5' homology arm, a DNA insert, and a 3' homology arm. CRISPR-based gene editing can generate gene knockouts by disrupting the gene sequence, however, efficiency for inserting exogenous DNA (knock-in) or replacement of genomic sequences is very poor using current methods.[33] In certain embodiments, CiSSDs may be used with CRISPR by generating a knock-in modification.

Double-stranded breaks can be introduced by any suitable mechanism, including, for example, by gene-editing systems using CRISPR,[32,33] zinc finger nuclease, TALEN nuclease (Transcription Activator-Like Effector Nuclease),[37] or meganuclease[38] as described previously.

Briefly, the CRISPR genome editing system generates a targeted DSB using the CRISPR programmable DNA endonuclease that can be targeted to a specific DNA sequence (target sequence) by a small "guide" RNA (crRNA).[32] Guide RNAs for use in CRISPR-based modification (i.e., crRNAs and tracrRNAs) may be generated by any suitable method. In certain embodiments, crRNAs and tracrRNAs may be chemically synthesized. In other embodiments, a single guide RNA (sgRNA) may be constructed and synthesized by in vitro transcription.

The CRISPR system can be further engineered to introduce a single-stranded DNA break, i.e., a nick.[39] Zinc finger nucleases (ZFNs) can be engineered to bind to a specific DNA sequence, and a DSB is introduced by a fused FokI (or other suitable DNA cutting domain) to cut one strand of DNA, subsequently, a pair of ZFNs introduce a DSB. Each finger recognizes a specific sequence of DNA, and fingers are fused together to target a longer target sequence. TALENs function similar to ZFNs, wherein an engineered TAL is fused to FokI (or other suitable DNA cutting domain). TAL binds to the target sequence, and multiple TALs can be fused together to target a longer sequence. Meganucleases function in a fashion similar to restriction enzymes to generate a DSB at a particular target site.

In step (c), the 5' homology arm and the 3' homology arm of the CiSSD are hybridized with the complementary polynucleotides in the target region of the genomic DNA. In certain embodiments, the homology arms are at least 50 nt in length. In certain embodiments, homology arms may range from 100 nt to 1000 nt in length or 50 nt to 3000 nt in length. In a preferred embodiment, the homology arms are approximately 200 nt to 400 nt, e.g., about 300 nt, in length.

In step (d), the DNA insert is inserted into the target region of genomic DNA. In some embodiments, the DNA insert is inserted into the target region of genomic DNA by homology directed repair (HDR). "Homology-directed repair" or "HDR", as used herein refers to the process of repairing DNA damage using a homologous nucleic acid (an exogenous nucleic acid, e.g., a template nucleic acid). HDR utilizes DNAs that contain homology sequences (the 5' homology arm and the 3' homology arm) flanking the DSB to template the repair. In embodiments provided herein, the 5' homology arm and the 3' homology arm are complementary to homology sequences flanking the DSB. In embodiments provided herein, the DNA insert is flanked by the 5' homology arm and the 3' homology arm and binds to the homology regions after the DSB is generated. Two homologous recombination based cross-overs occur in the 5' homology arm and the 3' homology arm regions, the crossover gets resolved in the homologous region. Thus, insert gets inserted into the genome. The cellular HDR machinery uses the DNA insert to provide a template for second strand synthesis to repair the DSB and the edit is incorporated at the target site.[32]

In one preferred embodiment, an optional step (e) is included. In step (e), one or more cells having the DNA insert is selected. Selecting the one or more genetically modified cells having the DNA insert may involve identifying a marker or a reporter (e.g., a fluorescent marker) encoded by the DNA insert. In some embodiments, selecting the or more genetically modified cells having the DNA insert may involve identifying whether the cell is resistant to a particular antibiotic, wherein the DNA insert encodes resistance to the particular antibiotic.

In accordance with the present invention, CiSSDs described herein have a greater integration efficiency of integrating its DNA insert into the cell than that of a LiSSD having a similar DNA insert length. In some embodiments, the CiSSD integration efficiency is about 10% to about 100% greater than the LiSSD integration efficiency, such as about 10% greater, about 20% greater, about 30% greater, about 40% greater, about 50% greater, about 60% greater, about 70% greater, about 80% greater, about 90% greater, or at least about 100% greater. Furthermore, the present invention using CiSSDs as a donor have a good specificity, low cytotoxicity and low off target effects. The CiSSD templates can be generated using fast, reliable, cost-effective, scalable, adjustable, and clonal methods.

CiSSDs for use in the present invention can be made by any suitable method known to one of skill in the art. Suitable methods may include CircLigase™ ssDNA ligase (Lucigen, USA) and previously described methods.[16,17,34] In certain embodiments, CiSSDs can be made by using a splint oligo to bridge two ends of linear DNA and subsequently ligate the ends with T4 ligase, as would be apparent to one of skill in the art.

In certain embodiments, CiSSDs can be made by using a recombinase (e.g., FLP or CRE) and partial duplex DNA which contains binding sites for FLP or CRE. For example, in certain embodiments a linear ssDNA may be used, wherein the ends of the linear ssDNA include a recombination site (e.g., FRT). Next, oligos are annealed to generate partial duplex DNA wherein the recombination sites are in the duplex region of DNA. Next, a recombinase, e.g., FLP is used to promote recombination between the two recombination sites (e.g., FRT) to generate a circular ssDNA (CiSSD) with a partial duplex region.

In certain embodiments, CiSSD can be made using a phagemid vector with the M13-based system. These methods include, but are not limited to, constructing and cloning donor inserts into phagemid vectors, such as pScaf.[16] While pScaf of known sequences can be used with the M13-based methods, pScaf can also be modified, for example, at least at one cis sequence, or at more than one cis sequence. These modifications can include about 1 nt, about 2 nts, about 3 nts, about 4 nts, about 5 nts, about 6 nts, about 7 nts, about 8 nts, about 9 nts, about 10 nts, about 20 nts, about 30 nts, about 40 nts, or about 50 nts which differ from the known pScaf sequence. By modifying pScaf to include one or more modified cis sequences, the present inventors recognized that homogeneity across a length of each CiSSD can be increased, such as by about 90%, about 95% or about 99%.

In certain embodiments, a bacteriophage-based system may be used.

In certain embodiments, an M13-based system is used and the CiSSD may include an initiator sequence and a terminator sequence. In certain embodiments of an M13-based system, the CiSSD may include an M13 packaging sequence and an initiator sequence and a terminator sequence from the M13 origin of replication.

Methods useful for constructing and cloning donor inserts are described elsewhere.[16] Donor inserts can be propagated in E. coli strains for clonality and molecular screening[19] and, recombinant CiSSD having these inserts can be generated using a helper plasmid. While any suitable helper plasmid can be used, examples include M13cp as well as those previously described.[17,20] An example phagemid includes, but is not limited to p67PCG. CiSSDs having the donor insert of interest can be purified as donor templates by extracting isolated phage particles. Suitable extraction methods are described elsewhere.[9] While any suitable E. coli strain can be used, examples include, but are not limited to XL1-Blue and DH11S. Other suitable E. coli strains having F pilus can also be used.

The genetically modified cells produced by the present method may be used in a cell therapy, e.g., a CAR-T cell therapy. In CAR T-cell therapy,[25,26] a large population of modified cells must be generated quickly for clinical application. Using conventional methods, cytotoxic effects deplete the T-cell population during modification and delay achieving a critical mass of modified cells. In embodiments provided herein, cytotoxicity of CiSSDs in human primary T-cells during CRISPR knock-in experiments will may be reduced.

In certain embodiments, the cell to be modified may be a human cell. In some embodiments, the cell may be T cell. In other embodiments, the cell may be a natural killer (NK) cell or a macrophage. In certain embodiments, the genetically modified cells are stem cells. In some embodiments, the genetically modified cells are non-human embryonic stem cells, non-embryonic stem cells (e.g., hematopoietic stem cells), induced pluripotent stem cells (iPSCs), cord blood stem cells, amniotic fluid stems cells, or any combination thereof.

In certain embodiments, the cells are T cells. In certain embodiments, the cells are natural killer (NK cells). In some embodiments, the T cell is a CD4+ T cell, a CD8+ T cell, a CD4− CD8− double negative T cell, an NK cell, or any combination thereof. In some embodiments, the T cell is a naïve T cell, a central memory T cell, a stem cell memory T cell, an effector memory T cell, an NK cell or any combination thereof.

In some embodiments, the insert encodes a chimeric antigen receptor (CAR). In some embodiments, the genetically modified cells are CAR-modified T cells. In some embodiments, the genetically modified cells are CAR-modified NK cells, CAR-modified macrophages, or CAR-modified hematopoietic cells. In certain embodiments, the cell to be modified may be a human cell.

In certain embodiments, an insert may include a gene coding region to genetically modify a cell. In certain embodiments, an insert may disrupt function of a gene on one or more alleles. Bi-allelic modification may benefit from increased efficiency of CiSSD donors, and the lower cytotoxicity with T cells underscores the value of CiSSDs to human health applications. These modified T cells are currently being assessed for improved immunotherapy as reflected by surrogate cellular phenotypes.

Methods of the present technology also include treating a disease, disorder, or condition in a subject in need thereof by providing cellular therapy comprising cells genetically modified with a CiSSD, such as those described herein. The cells can be T cells and the DNA insert carried by the CiSSD can encode a chimeric antigen receptor (CAR). In these methods, the genetically modified cells can be CAR-modified T cells.

Methods of the present technology also include treating a disease, disorder, or condition in a subject in need thereof by providing gene therapy comprising cells genetically modified with a CiSSD, such as those described herein.

In some embodiments, the present invention also includes methods for genetically modifying one or more non-human embryonic stem cells with a CiSSD, such as those described herein. These embodiments can also include methods for generating one or more transgenic animals or non-human mammals by transferring the CiSSD genetically modified non-human embryonic stem cells into an inner cell mass and transferring an embryo generated at least in part from the one or more CiSSD genetically modified non-human embryonic stem cells into a subject.

The present invention is useful in treating a mammal subject, such as humans.

Taken together, these attributes of the present disclosure are beneficial for gene engineering applications such as, but not limited to, gene therapy (e.g., ex vivo and/or in vivo) and cell therapy (e.g., ex vivo) including HDR technologies involving CRISPR, zinc finger, TALEN nuclease (Transcription Activator-Like Effector Nuclease), and meganuclease.

Additional applications of genetically modified cells include, but are not limited to, transgenic animals. Advantages of the present methods include improved integration efficiency, limited off-target integration, and may reduce cytotoxicity.

Those of skill in the art will recognize that a wide variety of delivery mechanisms and additional therapeutic uses are also suitable for the present invention.

The following examples further illustrate the present invention. These examples are intended merely to be illustrative of the present invention and are not to be construed as being limiting.

EXAMPLES

Example 1. Generating CiSSD for HDR Donor Templates (Prophetic Example)

One method for making CiSSDs is illustrated in Example 1. CiSSDs are be produced generally as follows. Donor inserts are constructed and cloned into phagemid vectors,[16] propagated in E. coli strains for clonality and molecular screening,[19] produced as recombinant CiSSD with the presence of a helper plasmid,[17,20] and purified as donor templates by extraction of isolated phage particles.[9] E. coli strains that can be used include XL1-Blue and DH11S; however, other E. coli strains having F pilus can also be used. DH11 S exhibits almost no lysis during chronic infection with M13, and thus reduces the amount of bacterial genome contamination in M13 preparations relative to other strains.[21]

M13cp helper plasmid is used to avoid contamination from helper phage.[20] The phagemid vector pScaf[6] is used for cloning and was previously engineered to produce ssDNA scaffolds for DNA origami biofabrication. In these studies, pScaf shows product homogeneity due to a 'leaky' initiator and terminator at a second, partialfl-ori on the vector.[16] The intended full-length product comprises just 46-83% of the total ssDNA produced.[16] Homogeneity may be improved by modifying pScaf cis sequences and phagemid (e.g., p67PCG) is constructed by changing in pScaf to achieve greater than 95% length homogeneity among CiSSDs. These changes to the phagemid may enable production of custom CiSSDs in less than three weeks, including cloning steps. DNA quantities suitable for CRISPR experiments are obtained from 5 ml cultures.

M13 may be useful for generating CiSSDs having a large cargo capacity, e.g., greater than about 2 kb, relative to LiSSDs generated using in vitro methods. Three inserts of varying sizes, e.g., 4 kb, 8 kb, and 12 kb, is generated and cloned into the p67PCG phagemid. M13 is used to produce CiSSDs of increasing sizes from these inserts. Growth times may be reduced but can be offset by increasing the exogenous magnesium added.[27]

Construction of phagemid vector p67PCG: The phagemid vector p67PCG is constructed by cloning the M13 ssDNA initiator and the M13 ssDNA terminator from the dual fl-ori of the pScaf vector[16] into a vector, which has cloning sites with recognition sequences for several Type II restriction enzymes to enable constructing recombinant p67PCG using Golden Gate Assembly[22]. The terminator sequence includes the triple thymine variant from pScaf[6] in place of the Δ29 design of Specthrie et al. (1992).[28] The p67PCG vector is verified by DNA sequencing.

Cloning of single-stranded homology-directed repair templates (ssHDRTs): Donor template sequences are constructed as dsDNA and placed into the p67PCG vector by Golden Gate Assembly with enzymes.[22] The phagemid is made receptive by Type II restriction digestion of a digestion site between the ssDNA synthesis initiator and terminator sequences. Other reporter constructs such as those that have been described previously may also be used.[7] N-terminal GFP reporter constructs described by Li et al., 2017[1] are used with this technology. Specifically, three loci-specific constructs are used: RABIJA (pTR143; addgene #112012); CD4 (pTR152; addgene #112018), and CLTA (pTR153; addgene #112016). Additional recombinant p67PCG phagemids are constructed with insert sizes of 4 kb, 8 kb, and 12 kb to test limits of cargo capacity with the M13 system.

Recombinant phagemid production and CiSSD purification: An XL1-Blue-MRF' Helper Strain (XL1Black) by transformation with the M13cp helper plasmid is generated.[20] Chemically competent cells are made with TSS (10% PEG-8000, 30 mM MgCl2, 5% DMSO, in 2×YT, pH 6, filtered). XL1Black are transformed with p67PCG+insert to create phage-producing cultures. Clones is selected and grown for 18 hours (30° C., 225 rpm) in 3 mls of 2×YT media (1.6% tryptone, 1% yeast extract, 0.25% NaCl) with kanamycin (50 μg/ml), carbenicillin (100 μg/ml), and chloramphenicol (25 μg/ml). The 3 ml starter culture is used to inoculate 100 ml of 2×YT, 10 ml phosphate buffer (7% potassium phosphate dibasic, 3% sodium phosphate monobasic, pH 7, autoclaved), 1 mL 50% glucose, 0.5 mL 1 M $MgCl_2$, and the same three antibiotics. The culture is grown for another 24 hours (30° C., 225 rpm).

The culture is transferred to a centrifuge bottle and incubated on ice for 30 minutes. The bacteria is pelleted by centrifugation at 7,000 g for 15 min at 4° C. The supernatant containing phage particles is transferred to another centrifuge bottle containing 4 g of PEG-8000 and 3 g of NaCl. The bottle is vortexed and incubated on ice for 30 minutes. The precipitated phage particles is pelleted by centrifugation at 9,000 g for 15 minutes at 4° C. The pellet is resuspended in 3 ml TE buffer and centrifuged again to remove any residual cellular debris (15,000 g for 15 minutes at 4° C.). The supernatant is transferred to a 50 ml conical tube containing 6 mls of Lysis Buffer (0.2M NaOH, 1% SDS) and vortexed. 4.5 ml of Neutralization Buffer (3M KOAc, pH 5.5) is added, vortexed again, and incubated on ice for 15 minutes. The mixture is centrifuged at 15,000 g for 15 minutes at 4° C. The supernatant is transferred to a 50 ml conical tube containing 27 mls of reagent-grade ethanol. The contents are mixed by inversion, and placed at −20° C. overnight.

The DNA precipitate is pelleted by centrifugation at 16,000 g for 15 minutes at 4° C. The pellet is washed with 9 ml of ice-cold 70% ethanol, and centrifuged at 16,000 g for 5 minutes at 4° C. The pellet is allowed to air dry 5-10 minutes before resuspension in 1 ml of low TE. Approximately 1 μg/ml of CiSSD is produced at this volume.

The concentration of CiSSDs is determined by Nanodrop for ssDNA and yields are 10 μg per ml of liquid culture. Ratios of Absorbance (A260 nm/280 nm and 260 nm/230 nm) will reflect consistent purity (1.8 and >2, respectively) from serial preps. Recombinant CiSSD is verified by DNA sequencing using custom-designed staggered sequencing primers for complete coverage. The DNA is adjusted to a standard concentration (1 μg/μl) in TE and stored at −20° C.

Alternate Method Contaminating chromosomal DNA in phagemid preps: M13 causes a chronic rather than lytic infection. Still, some bacterial host strains, including XL1-Blue, release contaminating chromosomal DNA into the supernatant at detectable levels. E. coli strain DH11S has been engineered to overcome this problem.[21] In some cases, XL1-Blue is used as host. In these cases, the differential renaturation rates of the DNA molecules (small ssDNA and large chromosomal dsDNA) is exploited to remove contaminating genomic DNA.

Alternate Method Transmission electron microscopy of virions: Recombinant phage particles are visually inspected for size homogeneity. Prior to imaging, supernatant aliquots (5 μL) from each M13 preparation is applied. Electron micrographs are collected using an FEI TECNAI T12 transmission electron microscope using a using a 4 k×4 k charge-coupled device camera (UltraScan 4000, Gatan) at 26000× and 52000× magnifications. Class averages are obtained using EMAN2 software.

Alternate Method Nucleotide Length Homogeneity of CiSSD: An aliquot of CiSSD (5 μl of 1 μg/μl) is linearized with PfAgo by digestion that was guided by synthetic 5'-phosphorylated, small interfering DNAs (siDNAs).[29] PfAgo is incubated with guide siDNA (15-31 nt long) and target ssDNA in a 5:1:1 ratio. The mixture is incubated at 75° C. for 1 hour, with 0.5 mM $Mn^{+2}$ as cation co-factor. Alternatively, restriction digestion is used with the help of a duplex-forming oligonucleotide spanning the enzyme's recognition sequence. After linearization, terminal transferase is used to covalently add a BigDye™ Terminator "A" to the 3' end. Variation in length of linearized CiSSD is measured under standard denaturing conditions with a sequencing instrument (ABI 3730) and POP7 polymer.

Alternate Method Superhelicity of CiSSD: The proportion of CiSSD and linearized ssDNA produced from nicked CiSSD is measured by DNA staining with SYBR® Gold (Thermo Fisher) and electrophoresis on 2% agarose gels. Superhelical circular molecules migrate faster than linear molecules of the same size and sequence. The re-circularized form of CiSSDs that is produced for experiments is re-confirmed. These molecules are relaxed circles that migrate slower during electrophoresis than either supercoiled circular ssDNA.

Alternate Method EliminatingM13 sequences from ssDNA clones: CiSSDs contain M13 sequences essential for synthesis and packaging. In some instances, these sequences are excised and the linearized CiSSD donor clone is isolated by both negative and positive purification. First, pairs of siDNA guides are designed to target two single-stranded cleavage events bracketing M13 cis-sequences. PfAgo is used to cut at both positions. PfAgo is incubated with two guide siDNAs (both 21 nt long) as well as the phagemid template CiSSD in a 5:1:1 molar ratio. The mixture is incubated at 75° C. for 1 h, with 0.5 mM $Mn^{+2}$. Double cleavage will produce two linear derivatives from the CiSSD: one with M13 sequence and the other with donor template sequence. Singly cut CiSSDs at either site is linearized, but both sequences are retained.

Streptavidin-coated magnetic beads (MyOne™ Streptavidin C1, Thermo Fisher) and a biotinylated 60-mer synthetic oligonucleotide of the complementary (−) strand sequence to base pair with the (+) strand M13 sequence of the CiSSD is used. The hybridization protocol is used for both negative and positive purification of ssDNA.

The streptavidin-coated beads are resuspended by vortexing and washed three times with 1 volume washing buffer. The beads are resuspended in 2× B&W Buffer to a final concentration of 5 μg/μl. An equal volume of biotinylated oligonucleotide in water is added to immobilize the oligo on the beads. The mixture is incubated for 15 min at room temperature with gentle rotation. The mixture is washed three times with 1× B&W Buffer, and then resuspended to 2.5 μg/μl (bead concentration).

Cleaved CiSSD DNA is mixed with the immobilized capture sequences at a 1:5 ratio in a PCR tube as 1 mg of Dynabeads binds 500 pmol of biotinylated oligonucleotide. The contents is brought to 65° C. with a −5° C. per minute ramp-down to 23° C., and then held for 20 min. Donor template sequences will remain in the supernatant, which is transferred to a new tube after magnetically separating the beads for 15 minutes. The nucleic acid in the supernatant is ethanol precipitated, washed, and then resuspended in 50 volume of low TE. A second round of hybridization-based capture is used to positively enrich donor template sequences, essentially as before except with a biotinylated oligonucleotide (60mer) complementary to the donor sequences. Final yields will recover about 25% of the original CiSSD concentration.

Alternate Method Nucleic acid purification with magnetic beads: Magnetic beads for nucleic acid purification is prepared as described previously.[30] Working solutions (50 ml) is prepared as follows: 1 ml carboxylate-modified magnetic bead solution (GE Healthcare #65152105050250) is washed with 3×1 ml RNase-free TE buffer (10 mM Tris, 1 mM EDTA, pH 8.0) on a magnetic stand. The bead pellet is resuspended in DNA precipitation buffer (RNase-free): (1 M NaCl; 10 mM Tris-HCl pH 8.0; 1 mM EDTA; 18% w/v PEG8000 (Sigma BioUltra); 0.05% v/v Tween20 (Sigma)). Magnetic beads in precipitation solution is added to nucleic acid samples in appropriate ratios and incubated for 10 min at RT. Bead-bound nucleic acids is immobilized with a magnet and washed 2× in RNase-free 70% EtOH. Beads are air-dried for 5-10 min at RT and the nucleic acids eluted in RNase-free $H_2O$.

Alternate Method A scalable purification scheme for CiSSD: Methods and compositions for selective nascent polymer catch-and-release enables scalable isolation of multi-kilobase ssDNA is used, and optionally modified, for scalable purification of CiSSD.[31]

Example 2 (Working Example)

Figure 2:
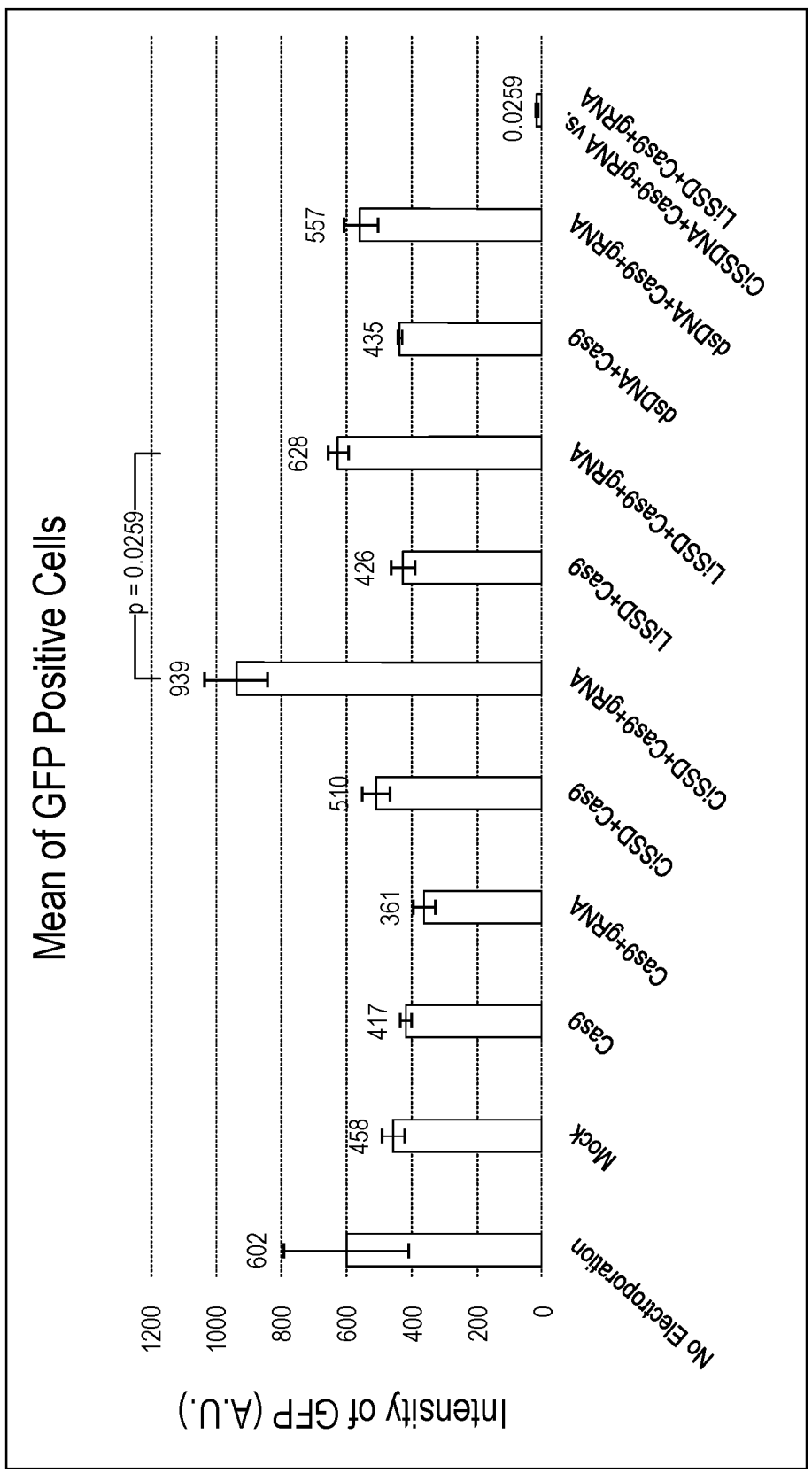
FIG. 2 is a chart showing the geometric mean of GFP positive cells in the noted conditions to compare CiSSD vs LiSSD. GFP intensity is measured in A.U.
Figure 3:
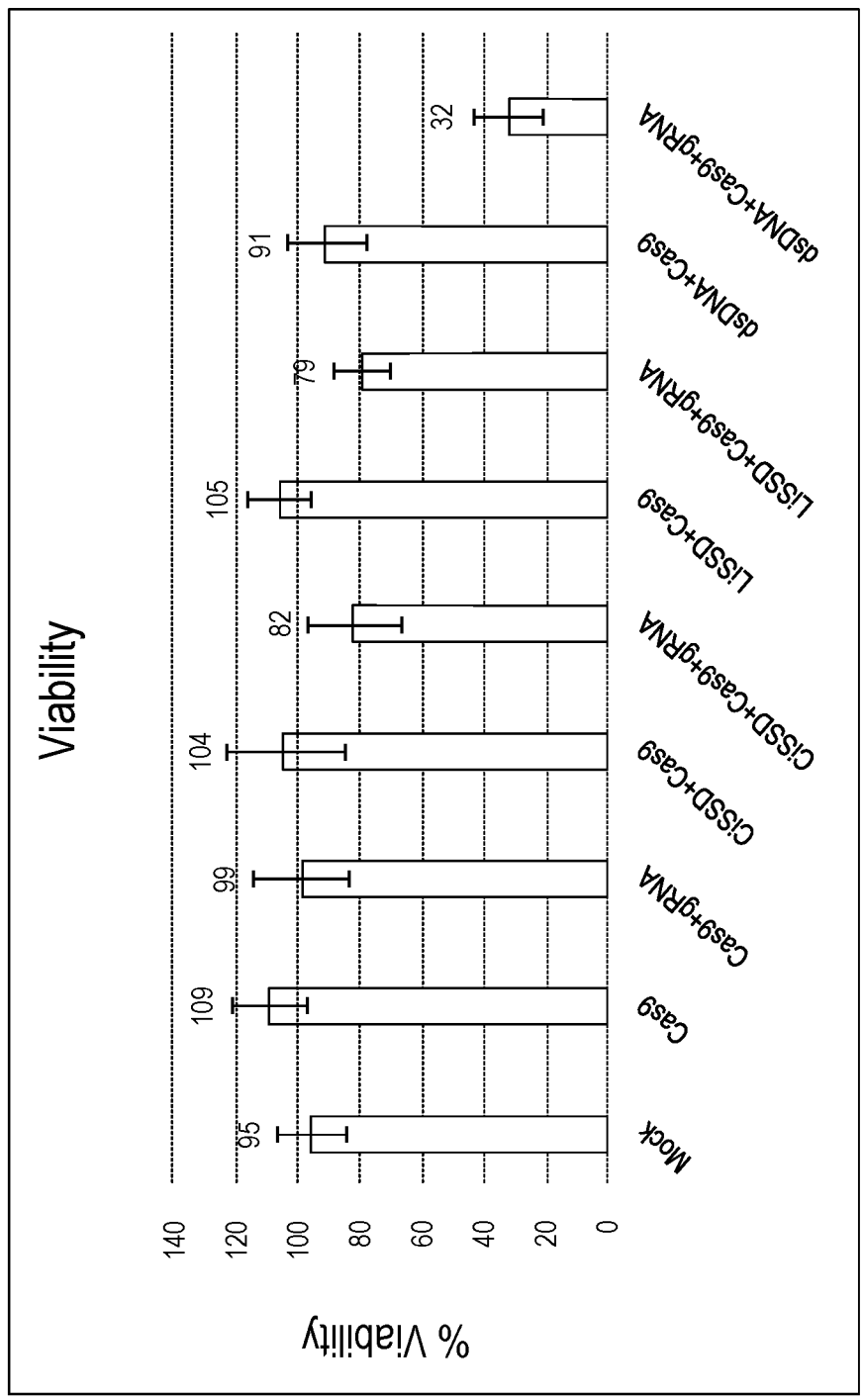
FIG. 3 is a chart showing the percent viability of cells under each noted condition.

The goal was to demonstrate that CiSSD could serve as superior DNA donor templates than LiSSD. As a proof of concept, a donor template resulting in N-terminal GFP fusion of RAB11A was used as previously described[7]. This donor template was composed of 306 bp of the left homology arm, GFP coding sequence, and 315 bp of the right homology arm. For induction of DNA double strand break, an sgRNA targeting 5'-GGTAGTCGTACTCGTCGTCG-3' (SEQ ID NO: 1) followed by a protospacer adjacent motif (PAM) sequence and *Streptococcus pyogenes* Cas9 protein with two nuclear localization signals (2NLS) were purchased (Synthego, USA). As a model organism, 293FT cells were used to test insertion efficiency and cell viability. The donor template was synthesized by polymerase cycling assembly and cloned into a vector. LiSSD was produced by enzymatically digesting one strand of DNA from PCR amplified double stranded DNA. First, linear double stranded DNA was amplified by PCR using Q5@ High-Fidelity DNA Polymerase (NEB, USA) with forward primer (GGTAGCTAGGAGTTCCAGGAC) (SEQ ID NO: 2) and reverse primer (/5Phos/ACGATGTGG-GAGAAGGCAGTC) (SEQ ID NO: 3). A phosphorylated strand was degraded by Guide-it™ Long ssDNA Production System (Takara, USA) to form linear single stranded DNA. Finally, CiSSD was extracted from M13 phage encoding the sequence of interest and single M13 origin of replication. Briefly, the sequence of interest was cloned into a vector between two wild type M13 origins of replication. It was then integrated in the genome of *E. coli* XL1-Blue at icd gene using CRIM system,[35,36] and M13 helper plasmid lacking the M13 packaging signal was transformed. The resulting *E. coli* produced a clonal population of M13 phages encoding the sequence of interest and single M13 origin of replication. It was grown overnight in 2×YT media at 37° C., and circular single stranded M13 phage genome was purified from M13 phages as previously described[16]. M13 phage genome purified by ethanol precipitation was dissolved in $H_2O$ for transfection into 293FT. For comparison of CiSSD and LiSSD in 293FT, Neon transfection system (Thermo Fisher Scientific, USA) was used. 293FT cells were maintained in DMEM supplemented with 10% FBS and incubated at 37° C. with 5% $CO_2$. 293FT cells were trypsinized and washed once with the same volume of PBS. Then cells were resuspended in R buffer (Thermo Fisher Scientific, USA). Per electroporation, 12.5 pmol of purified Cas9 and 50 pmol of sgRNA were mixed for 10 minutes at room temperature in 5 uL of R Buffer. For Cas9 without sgRNA, sgRNA was replaced with the same volume of TE buffer (10 mM Tris-HCl, 1 mM EDTA). It was then mixed with DNA donor templates and 5 uL of R buffer containing 150,000 cells of 293FT and electroporated using the following parameters: 1150 V/20 ms/2 pulses. Electroporated cells were seeded in 1 mL of pre-warmed DMEM supplemented with 10% FBS in 24 well plate. After 4 days, cells were trypsinized with 200 uL of trypsin and stabilized by adding 600 uL of phenol red free DMEM supplemented with 10% FBS. 400 uL of the cell suspension was washed once with PBS, and live and dead cells were stained with Ready-Probes™ Cell Viability Imaging Kit, Blue/Red (Thermo Fisher Scientific, USA) before analyzed by flow cytometry using BD Accuri™ C6 Flow Cytometer. The efficiency of DNA donor template was calculated by measuring percentage of GFP positive cells, as only cells with correctly integrated donor template sequences were producing GFP-RAB11A fusion protein. Geometric mean of intensity of GFP was measured from GFP positive cells from each sample. Indeed, CiSSD+Cas9+gRNA had higher efficiency than LiSSD+Cas9+gRNA (FIG. 1) and CiSSD+Cas9+gRNA has significantly stronger intensity than LiSSD+Cas9+gRNA (FIG. 2). To measure viability, a total number of cells from each sample was measured by Countess II FL Automated Cell Counter (Thermo Fisher Scientific, USA). From flow cytometry data, percent live cells were determined by counting live cells determined by ReadyProbes™ Cell Viability Imaging Kit, Blue/Red (Thermo Fisher Scientific, USA). Then total numbers of live cells for each sample were determined by multiplying the total number of cells counted using Countess II FL Automated Cell Counter by percent viability determined by flow cytometry. Finally, total numbers of live cells were normalized to 'No electroporation' samples to calculate viability showing in FIG. 3. Viability of CiSSD+Cas9+gRNA and LiSSD+Cas9+gRNA were similar but significantly have higher viability than dsDNA (plasmid DNA)+Cas9+gRNA.

It is to be understood that the foregoing describes preferred embodiments of the present invention and that modifications may be made therein without departing from the scope of the present invention as set forth in the claims.

REFERENCES

1. Li, H. et al. Design and specificity of long ssDNA donors for CRISPR-based knock-in. bioRxiv (2017).
2. Codner, G. F. et al. Application of long single-stranded DNA donors in genome editing: generation and validation of mouse mutants. BMC Biol 16, 70 (2018).
3. Lanza, D. G. et al. Comparative analysis of single-stranded DNA donors to generate conditional null mouse alleles. BMC Biol 16, 69 (2018).
4. Miura, H., Quadros, R. M., Gurumurthy, C. B. & Ohtsuka, M. Easi-CRISPR for creating knock-in and conditional knockout mouse models using long ssDNA donors. Nat Protoc 13, 195-215 (2018).
5. Xiao, Q. et al. Intracellular generation of single-strand template increases the knock-in efficiency by combining CRISPR/Cas9 with AAV. Mol Genet Genomics 293, 1051-1060 (2018).
6. Du, J. et al. Quantitative assessment of HR and NHEJ activities via CRISPR/Cas9-induced oligodeoxynucleotide-mediated DSB repair. DNA Repair (Amst) 70, 67-71 (2018).
7. Roth, T. L. et al. Reprogramming human T cell function and specificity with non-viral genome targeting. Nature 559, 405-409 (2018).
8. Dokshin, G. A., Ghanta, K. S., Piscopo, K. M. & Mello, C. C. Robust Genome Editing With Short Single-Stranded and Long, Partially Single-Stranded DNA Donors in Caenorhabditiselegans. Genetics (2018).
9. Vieira, J. & Messing, J. Production of single-stranded plasmid DNA. Methods in Enzymology 152, 3-11 (1978).
10. Hindley, J. & Phear, G. A. Sequencing long DNA fragments cloned in bacteriophage M13 by using internal primers. The sequence analysis of a yeast DNA fragment containing a replication origin. Biochem J 199, 819-823 (1981).
11. Messing, J. & Vieira, J. A new pair of M13 vectors for selecting either DNA strand of double-digest restriction fragments. Gene 19, 269-276 (1982).
12. Norris, K., Norris, F., Christiansen, L. & Fiil, N. Efficient site-directed mutagenesis by simultaneous use of two primers. Nucleic Acids Res 11, 5103-5112 (1983).
13. Zoller, M. J. & Smith, M. Oligonucleotide-directed mutagenesis using M13-derived vectors: an efficient and general procedure for the production of point mutations in any fragment of DNA. Nucleic Acids Res 10, 6487-6500 (1982).
14. Barbas, C. F., Burton, D. R., Scott, J. K. & Silverman, G. J. Phage Display: A Laboratory Manual (Cold Spring Harbor Laboratory Press, New York, 2001).
15. Nam, K. T. et al. Virus-enabled synthesis and assembly of nanowires for lithium ion battery electrodes. Science 312, 885-888 (2006).
16. Nafisi, P. M., Aksel, T. & Douglas, S. M. Construction of a novel phagemid to produce custom DNA origami scaffolds. bioRxiv (2018).
17. Tsedev, U. Engineering M13 Bacteriophage platforms for cancer therapy applications. Masters Dissertation, Department of Mechanical Engineering, MIT., 48 (2015).
18. Weiss, G. A. & Sidhu, S. S. Design and evolution of artificial M13 coat proteins. J Mol Biol 300, 213-219 (2000).
19. Dotto, G. P. & Horiuchi, K. Replication of a plasmid containing two origins of bacteriophage. J Mol Biol 153, 169-176 (1981).
20. Chasteen, L., Ayriss, J., Pavlik, P. & Bradbury, A. R. Eliminating helper phage from phage display. Nucleic Acids Res 34, e145 (2006).
21. Lin, J. J., Smith, M., Jessee, J. & Bloom, F. DH11S: an *Escherichia coli* strain for preparation of single-stranded DNA from phagemid vectors. Biotechniques 12, 718-721 (1992).
22. Engler, C., Kandzia, R. & Marillonnet, S. A one pot, one step, precision cloning method with high throughput capability. PLoS One 3, e3647 (2008).
23. Skene, P. J. & Henikoff, S. An efficient targeted nuclease strategy for high-resolution mapping of DNA binding sites. Elife 6, (2017).
24. Kosicki, M., Tomberg, K. & Bradley, A. Repair of double-strand breaks induced by CRISPR-Cas9 leads to large deletions and complex rearrangements. Nat Biotechnol 36, 765-771 (2018).
25. Gross, G., Waks, T. & Eshhar, Z. Expression of immunoglobulin-T-cell receptor chimeric molecules as functional receptors with antibody-type specificity. Proc Natl Acad Sci USA 86, 10024-10028 (1989).
26. Porter, D. L., Levine, B. L., Kalos, M., Bagg, A. & June, C. H. Chimeric antigen receptor-modified T cells in chronic lymphoid leukemia. N Engl J Med 365, 725-733 (2011).
27. Reddy, P. & McKenney, K. Improved method for the production of M13 phage and single-stranded DNA for DNA sequencing. Biotechniques 20, 854-6, 858, 860 (1996).
28. Specthrie, L. et al. Construction of a microphage variant of filamentous bacteriophage. J Mol Biol 228, 720-724 (1992).
29. Swarts, D. C. et al. Argonaute of the archaeon *Pyrococcus furiosus* is a DNA-guided nuclease that targets cognate DNA. Nucleic Acids Res 43, 5120-5129 (2015).
30. Rohland, N. & Reich, D. Cost-effective, high-throughput DNA sequencing libraries for multiplexed target capture. Genome Res 22, 939-946 (2012).

31. Krieg, E. & Shih, W. M. Selective Nascent Polymer Catch-and-Release Enables Scalable Isolation of Multi-Kilobase Single-Stranded DNA. Angew. Chem. Int. Ed. 57, 714-7718 (2018).
32. Paix et al. Precision genome editing using synthesis-dependent repair of Cas9-induced DNA breaks. PNAS E10745-E10754 (2017).
33. Miura et al. Easi-CRISPR for creating knock-in and conditional knockout mouse models using long ssDNA donors. Nature Protocols 13(1) 195-215 (2018).
34. Shepherd et al. Bioproduction of pure, kilobase-scale single-stranded DNA.
Scientific Reports 9(6121) (2019).
35. Haldimann, A. & Wanner, B. Conditional-Replication, Integration, Excision, and Retrieval Plasmid-Host Systems for Genetic Structure-Function Studies of Bacteria. J. Bacteriol. 183(21): 6284-6393 (2001).
36. U.S. Pat. Pub. No. 20070128728A1.
37. Gaj et al. ZFN, TALEN, and CRISPR/Cas-Based Methods for Genome Engineering. Trends in Biotech. 31(7): 397-405 (2013).
38. Silva et al. Meganucleases and Other Tools for Targeted Genome Engineering: Perspectives and Challenges for Gene Therapy. Curr. Gene Ther. 11(1): 11-27 (2011).
39. Ran et al. Double Nicking by RNA-Guided CRISPR Cas9 for Enhanced Genome Editing Specificity. Cell 154(6): 1380-1389 (2013).

homology arm to a cell, wherein the 5' homology arm and the 3' homology arm are complementary to the polynucleotides in a target region of a genomic DNA in the cell;
inducing a nucleotide break with Cas nuclease in the target region of genomic DNA in the cell;
hybridizing the 5' homology arm and the 3' homology arm of the CiSSD with the complementary polynucleotides in the target region of the genomic DNA; and
inserting the DNA insert into the target region of genomic DNA;
whereby a genetically modified cell is generated, and the CiSSD has a higher integration efficiency than that using a linear single stranded DNA under the same condition.

2. The method of claim 1, further comprising selecting one or more cells having the DNA insert.

3. The method of claim 1, wherein the nucleotide break is a double-stranded nucleotide break.

4. The method of claim 1, wherein the CiSSD further comprising an initiator sequence and a terminator sequence.

5. The method of claim 1, wherein the cell is a T cell or a natural killer cell.

6. The method of claim 1, wherein the DNA insert encodes a chimeric antigen receptor (CAR).

7. The method of claim 6, wherein the genetically modified cells are CAR-modified T cells.

What is claimed is:

1. A method for generating a genetically modified cells, comprising:
transferring a circular single stranded DNA (CiSSD) having a DNA insert, a 5' homology arm, and a 3'

8. The method of claim 6, wherein the genetically modified cells are CAR-modified natural killer cells.

9. The method of claim 1, wherein the genetically modified cells are non-human embryonic stem cells.

10. The method of claim 1, wherein the insert is about 2 kB to 20 kB in length.

11. The method of claim 1, wherein the insert is about 2 kB to 10 kB in length.

12. The method of claim 1, wherein the insert is about 1.6 kB to 5 kB in length.

13. The method of claim 1, wherein the 5' homology arm and the 3' homology arm are each between about 50 nucleotides to 3000 nucleotides in length.

14. The method of claim 13, wherein the 5' homology arm and the 3' homology arm are each about 300-500 nucleotides in length.

* * * * *